(12) United States Patent
Datovech et al.

(10) Patent No.: US 9,510,762 B2
(45) Date of Patent: Dec. 6, 2016

(54) ELECTRODE ARRAYS

(71) Applicant: LKC Technologies Inc., Gaithersburg, MD (US)

(72) Inventors: James J. Datovech, Gaithersburg, MD (US); Charles Quentin Davis, Frederick, MD (US); Bryan A. Hays, Damascus, MD (US); Anatolie Hobet, Salem, OR (US); Frank Hunleth, Rockville, MD (US)

(73) Assignee: LKC TECHNOLOGIES, INC., Gaithersburg, MD (US)

( * ) Notice: Subject to any disclaimer, the term of this patent is extended or adjusted under 35 U.S.C. 154(b) by 0 days.

(21) Appl. No.: 14/426,063

(22) PCT Filed: Sep. 4, 2013

(86) PCT No.: PCT/US2013/058007
§ 371 (c)(1),
(2) Date: Mar. 4, 2015

(87) PCT Pub. No.: WO2014/039525
PCT Pub. Date: Mar. 13, 2014

(65) Prior Publication Data
US 2015/0265173 A1    Sep. 24, 2015

Related U.S. Application Data (60) Provisional application No. 61/696,499, filed on Sep. 4, 2012.

(51) Int. Cl.
*A61B 5/0478* (2006.01)
*A61B 5/04* (2006.01)
(Continued)

(52) U.S. Cl.
CPC ......... *A61B 5/04001* (2013.01); *A61B 5/0478* (2013.01); *A61B 5/04085* (2013.01);
(Continued)

(58) Field of Classification Search
CPC .......... A61B 5/04085; A61B 5/04087; A61B 5/0478; A61B 5/0492; A61B 5/0476; A61B 2562/222; A61B 2562/227; A61B 5/04001; A61B 5/6814
See application file for complete search history.

(56) References Cited

U.S. PATENT DOCUMENTS 4,583,549 A * 4/1986 Manoli ................. A61B 5/411
                                                 600/391
4,763,660 A * 8/1988 Kroll ................. A61B 5/04085
                                                 439/77
(Continued)

FOREIGN PATENT DOCUMENTS

EP        1629768 A2    3/2006

OTHER PUBLICATIONS

International Search Report Issued in International PCT Application PCT/US2013/058007 dated Dec. 24, 2013.
(Continued)

*Primary Examiner* — Lee S Cohen
(74) *Attorney, Agent, or Firm* — Andrews Kurth Kenyon LLP; Sean S. Wooden (57) ABSTRACT

Electrode arrays have a plurality of electrodes. These arrays may have any combination of the following improvements. The arrays may have features that enable easier electrical connections and reduced bending stiffness by having a stop region and a torsion relief region, respectively. The arrays may have a shielding feature that may reduce electrical interference. The arrays may come in pairs that are designed to simplify measurements of electric signals of bilateral organs and tissues, such as eyes and ears.

13 Claims, 4 Drawing Sheets

(51) Int. Cl.
*A61B 5/0408* (2006.01)
*A61B 5/0492* (2006.01)
*A61B 5/0496* (2006.01)
*A61B 5/00* (2006.01)

(52) U.S. Cl.
CPC ........... *A61B5/0492* (2013.01); *A61B 5/0496* (2013.01); *A61B 5/6814* (2013.01); *A61B 5/6833* (2013.01); *A61B 2562/125* (2013.01); *A61B 2562/227* (2013.01)

(56) References Cited

U.S. PATENT DOCUMENTS

| | | | | |
|---|---|---|---|---|
| 5,042,481 A * | 8/1991 | Suzuki | ............... | A61B 5/04085 600/391 |
| 5,125,405 A * | 6/1992 | Schmid | ............. | A61B 5/04087 600/391 |
| 5,265,579 A * | 11/1993 | Ferrari | ............... | A61B 5/04085 29/825 |
| 5,327,888 A | 7/1994 | Imran | | |
| 5,772,591 A | 6/1998 | Cram | | |
| 6,032,064 A | 2/2000 | Devlin et al. | | |
| 6,233,472 B1 | 5/2001 | Bennett et al. | | |
| 6,453,186 B1 * | 9/2002 | Lovejoy | ............. | A61B 5/04085 600/386 |
| 6,564,079 B1 | 5/2003 | Cory et al. | | |
| 6,654,626 B2 * | 11/2003 | Devlin | ............... | A61B 5/04085 600/372 |
| 6,748,256 B2 * | 6/2004 | Brodnick | ............ | A61B 5/0408 600/382 |
| 6,865,409 B2 * | 3/2005 | Getsla | ................. | A61N 1/0452 128/902 |
| 7,206,630 B1 * | 4/2007 | Tarler | ................... | A61B 5/0006 600/393 |
| 8,971,983 B2 * | 3/2015 | Gilmore | ............... | A61B 5/0492 600/391 |
| 2001/0031916 A1 | 10/2001 | Bennett et al. | | |
| 2002/0177767 A1 | 11/2002 | Burton et al. | | |
| 2003/0130585 B2 * | 7/2003 | Wenger | | |
| 2004/0030258 A1 | 2/2004 | Williams et al. | | |
| 2007/0060975 A1 | 3/2007 | Mannheimer et al. | | |
| 2009/0281451 A2 | 11/2009 | Hetling et al. | | |

OTHER PUBLICATIONS

Supplementary European Search Report dated May 12, 2016 for EP 13834778.

* cited by examiner

ELECTRODE ARRAYS

RELATED APPLICATIONS

This application is a national stage application under 35 U.S.C. §571 based on PCT Application No. PCT/US2013/058007, entitled "Electrode Arrays" and filed Sep. 4, 2013, which claims the benefit of U.S. Provisional Application Serial No. 61/696,499, entitled "Electrode Arrays" and filed Sep. 4, 2012. The entirety of the aforementioned applications are incorporated herein by reference.

GOVERNMENT RIGHTS

Inventions described herein were made with government support under grant 9R44EY021121 awarded by the National Institutes of Health, USA. Accordingly, per the terms and conditions of the grant, the U.S. government has certain license rights in the present application.

FIELD

Embodiments of the present invention relate to improved electrode arrays. These electrode arrays can be used to monitor physiological electric signals.

BACKGROUND

Electrodes can be used to monitor physiological electric signals on the skin of a patient. These signals may come from, for example, muscle, nerves, the heart, the brain, the ear, or the eye. Monitoring electric signals from a patient can be used, for example, to determine the health of various organs and organ systems. Applications include, but are not limited to electrocardiograms, electroretinograms, nerve conduction testing, electroencephalograms, electrogastrograms, and evoked potential measurements from optical, acoustic, tactile, thermal, olfactory, and taste stimulation.

One of the difficulties in monitoring physiological electric signals on the skin is the inconvenience and variability caused by have to place many electrodes separately. To overcome this difficulty, electrode arrays have been employed (e.g., U.S. Pat. Nos. 5,722,591; 6,032,064; and 6,564,079).

There still exists a need to make electrode arrays that are easier to use and/or have improved performance.

SUMMARY

In one embodiment, an electrode array is disclosed. The electrode array includes at least two hydrogel islands. At least two of the hydrogel islands have a corresponding electrode contacting said hydrogel island. The electrode array also has a flexible insulating substrate that includes an electrode region, a torsion relief region, and a connector region. The electrode array also comprises conductors located on said substrate that electrically connect the electrodes to the connector region. In these embodiments, all the electrodes are located in the electrode region. The connector region and the electrode region may be connected together through the torsion relief region. The torsion relief region may be narrower than the connector region and may be connected to a long side of the electrode region, the long side of the electrode region being defined as the long side of the smallest rectangle that encloses all the electrodes. The connector region may include a tip region and a stop region, the tip region arranged at an edge of the electrode array and the stop region arranged adjacent to the tip region, the stop region being wider than the tip region. The electrode array can be used, for example, for monitoring physiological electric signals In accordance with another embodiment, an electrode array is disclosed. The electrode array includes a flexible insulating substrate having a first side and a second side. The substrate has an electrode region and a connector region. The electrode array has at least two of the hydrogel islands located on the first side of the substrate. At least two hydrogel islands have a corresponding electrode contacting said hydrogel island. Conductors located on the substrate electrically connect the electrodes to the connector region. A shield may be present. The shield may include a shield conductor adjacent to the second side of substrate, with the shield conductor covering at least half of the corresponding area on the second side of the substrate that the electrodes occupy of the first side the substrate. The electrode array can be used, for example, for monitoring physiological electric signals.

In accordance with another embodiment, a pair of electrode arrays is disclosed. The electrode array pair includes a first and a second electrode array. The first electrode array and the second electrode array both separately include a flexible insulating substrate that includes an electrode region and a connector region; at least two electrodes located in the electrode region; and conductors located on the substrate to electrically connect the electrodes to a set of contact locations in the connector region. In these embodiments, the contact locations in the first and second electrode array are in the same pattern so that one connector may alternatively make electrical connections to both electrode arrays; and the relation between contact locations and electrode locations on the second electrode array is a substantially mirror image to the relation between contact locations and electrode locations on the first electrode array. The pair can be used, for example, for monitoring physiological electric signals from the left and right sides of a human.

In accordance with another embodiment, a pair of electrode arrays is disclosed. The pair includes a first and a second electrode array. The first electrode array and the second electrode array both separately include a flexible insulating substrate that includes an electrode region and a connector region; at least two electrodes located in the electrode region; and conductors located on said substrate electrically connecting the electrodes to a set of contact locations in the connector region. The first electrode array has a first set of markings and the second electrode array has a second set of markings. The first set of markings is visually distinct from the second set of markings. The pair can be used, for example, for monitoring physiological electric signals from the left and right sides of a human.

Other embodiments include methods of using the electrode arrays described above to measure an electric signal from a patient, for example, a physiological electric signal. The method includes the steps of contacting the electrode array to the patient and measuring the electric signal from at least one electrode. The electric signal may be the potential difference between two electrodes in the electrode array.

Other embodiments include methods of using the pairs of electrode arrays described above to measure at least two electric signals from a patient, for example, two physiological electric signals. The method includes the steps of obtaining a pair of electrode arrays, contacting both electrode arrays to the patient, and measuring the electric signal from at least one electrode from each array. The electric signals may be the potential difference between two pairs of electrodes, where the members of each pair may or may not be on the same electrode array.

It is to be understood that both the foregoing general description and the following detailed description are exemplary and explanatory only and are not restrictive of the invention as claimed. The foregoing background and summary are not intended to provide any independent limitations on the claimed invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1c is an enlarged view of one portion of FIG. 1a.

DETAILED DESCRIPTION

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

Unless otherwise defined, scientific and technical terms used in connection with the present invention shall have the meanings that are commonly understood by those of ordinary skill in the art. Although any methods, devices, and materials similar or equivalent to those described herein can be used in the practice of the presently disclosed subject matter, representative methods, devices, and materials are now described. Further, unless otherwise required by context, singular terms shall include pluralities and plural terms shall include the singular.

As used herein, the term "hydrogel" refers to a nonfluid colloidal network or polymer network that is expanded throughout its volume by water. Hydrogel also refers to any electrically-conductive, water-comprising gel known in the medicinal, biofeedback, or biological testing arts. A hydrogel may comprise, for example, silicone, polyacrylamides, polyethylene oxide, polyAMPS, polyvinylpyrrolidone, polyvinyl alcohol, acrylate polymers, sodium polyacrylate, agarose, methylcellulose, or hyaluronan. A hydrogel optionally may contain mechanical strengthening members as well as the water-expanded colloidal network or polymer network. Further, a hydrogel is a "hydrogel island" if the hydrogel does not contact a second hydrogel. For example, one hydrogel is always a hydrogel island. As another example, three hydrogels, if mutually non-contacting, form three hydrogel islands.

As used herein, the term "patient" refers a human or other mammal from which electric signals are to be measured. It is contemplated that the electrode arrays of the invention will contact the patient to enable measurement of electric signals.

As used herein, the term "substrate" refers to a supporting material on which electrodes and conductors can be placed. A substrate may be, for example, a single sheet of plastic or a laminate of materials. The plastic used may be chosen from one or more (i.e., a combination) of the following: polycarbonate, cellulose, poly vinyl chloride (PVC), polypropylene, ABS, polyethylene, low density polyethylene, high density polyethylene, ultra-high molecular weight polyethylene, PTFE, acetal, polyester, PVDF, FEP, PFA, Ultem, PEEK, polyimide, garolite, polyethylene terephthalate (PET), and biaxially-oriented polyethylene terephthalate (boPET).

The improved electrode arrays, as well as additional objects, features, and advantages thereof, will be understood more fully from the following detailed description of certain preferred embodiments. These electrode arrays can be used to monitor physiological electric signals from the skin, for example, physiological electric signals. These signals may come from, for example, muscle, nerves, the heart, the brain, one or both ears, or one or both eyes. For bilaterally symmetric organs and tissues, a pair of electrode arrays may be advantageously used.

Figure 1A:
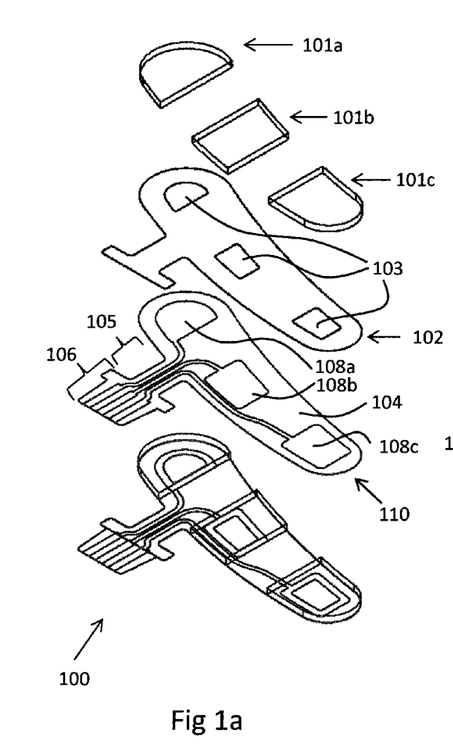
FIG. 1a is an exploded view of one embodiment of an electrode array, as seen from the patient side.
Figure 1B:
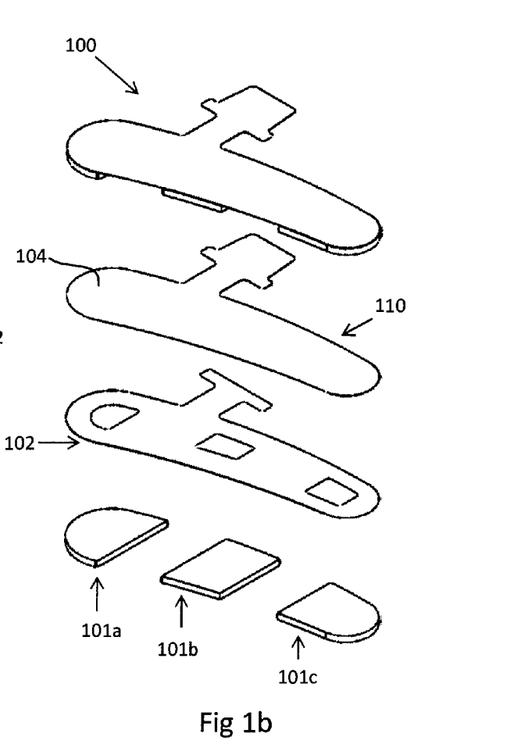
FIG. 1b is an exploded view of one embodiment of an electrode array, as seen from the operator side.
Figure 1C:
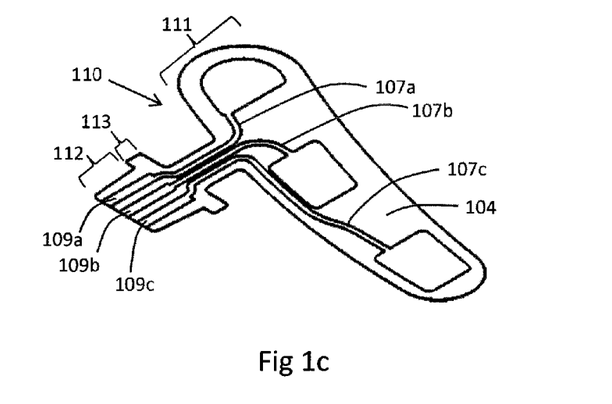

FIG. 1a and FIG. 1b are exploded views of one embodiment of an electrode array 100. FIG. 1c has an enlargement of a conductive layer 110 from FIG. 1a. In this example, the electrode array 100 includes a layer of hydrogel islands (101a, 101b, 101c), an optional insulating layer 102, and a conductive layer 110. Collectively, all the hydrogel islands may be referred to by the reference number 101. An insulating layer 102 has apertures 103 so that hydrogel islands 101a, 101b, 101c contact electrodes 108a, 108b, 108c, respectively. Collectively, all the electrodes may be referred to by the reference number 108. Electrodes 108 are located on the conductive layer 110. A conductive layer 110 has a flexible insulating substrate 104. The substrate 104 can be logically split into a connector region 106, a torsion relief region 105, and an electrode region 111, which is in this example the remainder of substrate 104. In FIG. 1c, the conductive layer 110 has conductors 107a, 107b, and 107c (collectively, 107) that electrically connect the corresponding electrodes 108a, 108b, and 108c through the torsion relief region 105 to the connector region 106. As an example, electrode 108a is connected to conductor 107a to contact location 109a in connector region 106. Contact locations 109b and 109c are analogously connected through conductors 107b and 107c to electrodes 108b and 108c, respectively.

Although three hydrogel islands (101a, 101b, 101c) and three electrodes (108a, 108b, 108c) are shown in FIG. 1a and FIG. 1b, other quantities are contemplated. For example, electrode 108b may be omitted. In this case, the corresponding hydrogel island 101b may or may not be omitted; hydrogel island 101b may still be useful to help adhere the electrode array 100 to a human subject. In other embodiments, four or more hydrogel islands may be used, at least two of which having corresponding electrodes. For example, an electrode array 100 may have 5, 10, 20, 50, or more electrodes.

An insulating layer 102 prevents hydrogel islands from contacting conductors that connect to electrodes other than those intended. When an insulating layer 102 is not used, vias may be used or smaller hydrogel islands may be used to route distant conductors to a connector region 106 (e.g., routing conductor 107c past hydrogel 101b).

When present, an aperture 103 may be larger than, smaller than, or equal to the size of an electrode 108. If an aperture 103 is smaller than its corresponding electrode 108, the aperture 103 defines the effective size that electrode. An aperture 103 may differ from the size of an electrode 108 in order to reduce the variability in electrode size due to manufacturing tolerances in the fabrication of the insulating layer 102 or the registration of the insulating layer 102 and the conductive layer 110.

In some embodiments, the hydrogel islands 101 contact a patient's skin during use to carry electric signals between the electrodes and the patient. Hydrogel islands 101 may also help an electrode array 100 adhere or otherwise stick to a patient's skin. Additionally, an electrode array 100 may include foam-backed adhesives, pressure-sensitive adhesives, or other materials that help the electrode array adhere or otherwise stick to a patient's skin, although no such substance is required or shown in FIG. 1.

In some embodiments, a torsion relief region 105 provides improved operation, as described hereafter. In operation, the electrode array 100 contacts a patient's skin. An electrode array 100 can be flexible so as to conform to the shape of the relevant portion of the patient's body. On the other hand, the connector region 106 will likely conform to the shape of an electrical connector that carries electric signals between electrode array 100 and attached instrumentation. In use, the shape in connector region 106 is unlikely to be the same shape as electrode region 111 when it is conforming to the shape of the contact region of the patient's body; accordingly, the electrode array 100 may bend. This bending may cause forces on the hydrogel islands 101 that reduces adherence to the patient's body and, therefore, affects the ability of the electrode array 100 to measure electric signals from the patient. The torsion relief region 105 is narrower than connector region 106 so as to reduce the bending stiffness and ameliorate this adherence issue. In various embodiments, torsion relief region 105 may have a width falling in a variety of ranges relative to the maximum width of the connector region 106. For example, the torsion relief region 105 may have a width less than 0.9, 0.8, 0.7, 0.5, 0.3, 0.2, or 0.1 times less than the maximum width of the connector region 106. Other ranges of width may be chosen as well. To reduce the effect of the weight of the electrical connector as the electrical connector possibly pulls away from the patient's skin, potentially peeling off a single hydrogel island, the torsion relief region is connected to a long side of the electrode region, the long side of the electrode region being defined as the long side of the smallest rectangle that encloses all the electrodes. Consequently, the weight of the connector is distributed more evenly across the hydrogels, assuming in operation the short side of the electrode region is more closely aligned to the gravitational direction than the long side of the electrode region.

The connector region 106 may include a tip region 112 and a stop region 113. An electrical connector used in operation may slide onto tip region 112. In some embodiments, the stop region 113 physically stops the connector from sliding further onto electrode array 100. In some embodiments, the stop region 113 provides visual feedback to the user that the connector is fully seated on electrode array 100. In some embodiments, the tip region 112 has tapered sides, as shown in FIG. 1, so as to make it easier for a connector to slide onto connector region 106. The tip region 112 may also have straight sides. The tip region 112 may have one or more holes or notches to aid in the alignment of a connector.

Electrodes 108 may be fabricated from metal or a semiconductor. Electrodes 108 in operation are able to convert a flow of electrons/holes into a flow of ions in hydrogel islands 101. Electrodes 108 may be fabricated from at least one of gold, silver, platinum, palladium, rhodium, nickel, carbon, indium, tin, or copper. Electrodes 108 may comprise at least one of gold, silver, or carbon. Electrodes 108 may comprise silver/sliver chloride. Electrodes 108 may be deposited on substrate 104 by any means known to the art, for example, by printing, silk screening, ink jet printing, sputtering, or printed circuit board fabrication methods. Electrodes 108 may be silkscreened silver, silver/silver chloride, carbon black, or carbon nanotubes. Having a large electrochemical surface area reduces the impedance and improves operation.

Conductors 107 may be fabricated from metal or a semiconductor. Conductors 107 may be fabricated from material that is the same or different than electrodes 108. Conductors 107 can be fabricated using the same types of methods used to fabricate electrodes 108. In some embodiments, conductors 107 are made from the same material and deposited on substrate 104 at the same time as electrodes 108. In some embodiments, conductors 107 are deposited first, and electrodes 108 are deposited on top of a portion of conductors 107. For example, conductors 107 may be silkscreened carbon black that is applied before a silver/silver chloride layer is applied to form electrodes 108. Alternatively, conductors 107 may be silkscreened silver that is applied before a carbon or silver/silver chloride layer is applied to form electrodes 108. In some embodiments, conductors 107 and electrodes 108 are silver/silver chloride fabricated using a silk screen process.

Conductors 107a, 107b, 107c may have corresponding contact locations 109a, 109b, 109c (collectively 109) in the connector region 106. Contact locations 109 may be wider than the conductors 107 so as to make a larger target for an electrical connector that connects to electrode array 100. Some of the edges of connector region 106 may form guides that help in positioning a connector to make electrical connection to contact locations 109. Contact locations 109 may be fabricated from metal or a semiconductor. Contact locations 109 may be fabricated a material that is the same or different than conductors 107. Contact locations 109 may be fabricated using the same types of methods used to fabricate conductors 109. In some embodiments, conductors 107 are deposited first, and contact locations 109 are deposited on top of a portion of conductors 107. For example, conductors 107 may be silkscreened carbon black that is applied before a silver or a gold layer is applied to form contact locations 109. In some embodiments, conductors 107 and contact locations 109 are silver/silver chloride fabricated using a silk screen process.

In some embodiments, electrodes 108 are substantially evenly spaced. In some embodiments, a ratio of the largest distance between adjacent electrodes to the smallest distance between adjacent electrodes is less than 3. In some embodiments, the ratio is less than 2. In some embodiments, the ratio is less than 1.5. The distance between adjacent electrodes is defined as the shortest line or curve traveling along the substrate where one of the endpoints of the line or curve is in one electrode and the other endpoint is in the other electrode.

Hydrogels 101 may include water and ions in a polymer matrix. Having a large surface area reduces the impedance to the skin and also increases the adherence of the hydrogels to the skin. Excessively large surface areas of hydrogels reduce the spatial resolution in electric signals. Hydrogels that are too sticky are uncomfortable upon removal from the skin, which is particularly important in cases where the electrode array is used on sensitive skin, such as below the eye. Hydrogels that are not sticky enough may lead to poor electrode array contact in embodiments where no other means of ensuring contact is provided. In some embodiments, the hydrogel islands have a peel strength to stainless steel of no more than 1500 grams per inch and no less than 100 grams per inch. In some embodiments, the hydrogel islands have a peel strength to stainless steel of no more than 1000 grams per inch and no less than 400 grams per inch.

In some embodiments, including the embodiment shown in FIG. 1, the electrodes are all located on one side of the substrate. Other embodiments may have electrodes on both sides.

Figure 2:
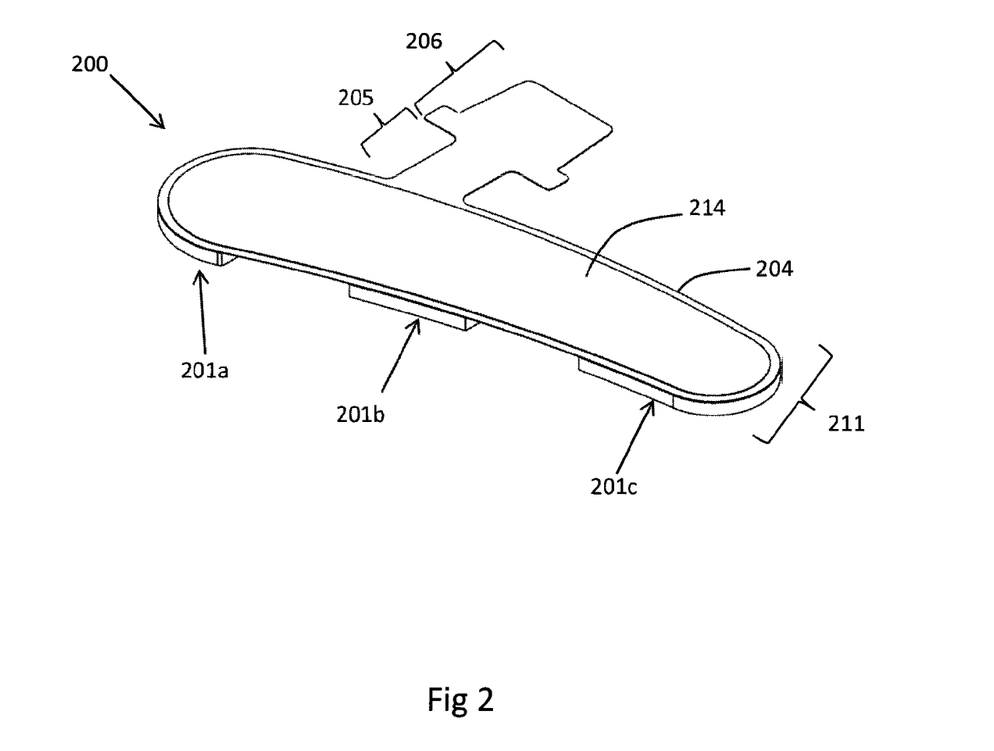
FIG. 2 is a view of one embodiment of an electrode array, as seen from the operator side.

Turning now to FIG. 2, electrode array 200 is another embodiment of the invention. Electrode array 200 has similar hydrogel islands 201a, 201b, 202c, as well as many of the other features of electrode array 100, including a flexible insulating substrate 204 having a connector region 206 and an electrode region 211. Electrode array 200 optionally has a torsion relief region 205, a connector region 206, including tip and stop regions, as well as other features in the above described electrode array 100. In some embodiments, only two hydrogel islands are required. Conductors on electrode array 200 are similar to those of electrode array 100. Electrode array 200 has a new feature: a shield comprising a shield conductor 214. The shield conductor 214 covers at least half of the corresponding area on the second side of substrate 204 that the electrodes occupy of the first side the substrate 204. The shield conductor 214 may be solid or it may include regions that have a mesh, comb, or hatch pattern. A mesh, comb, or hatch pattern may reduce the material cost of shield conductor 204 and may reduce the stiffness of electrode array 200 so that it will more easily conform to the patient during use. The area of the shield conductor 214 is defined to include the interior of any meshes or hatch patterns as well at the interdigitated space of any comb structures on in the shield conductor. As shown in FIG. 2, the shield conductor 214 may cover all the electrode area and most of the conductor area. Optionally, the shield conductor 214 may extend to the connector region and/or cover the entire second side of substrate 204. In some embodiments, the shield is simply the shield conductor 214.

As described for electrode array 100, electrode array 200 has conductors that connect electrodes in the electrode region 211 to the connector region 206. These conductors may be located on the same side as the electrodes, the opposite side, or on a combination.

Electrodes in electrode array 200 may be susceptible to interference capacitively-coupled in from the surroundings. A shield conductor 214 may reduce the capacitance of some or all the electrodes to the surroundings, making measurements with electrode array 200 cleaner by reducing outside interference. To perform this function, a shield conductor 214 may cover at least part of the electrodes. Conveniently, the shield conductor 214 may be deposited to the side of substrate 204 opposite that of the electrodes. Alternatively, the shield conductor 214 can form at least part of an additional layer that gets attached to the substrate 204. For example, the shield can be an adhesive-backed conducting layer or a conductive layer that is laminated to substrate 204.

The shield conductor 214 can optionally be connected to an electrode or can be disconnected from all the electrodes. For example, a shield conductor 214 may be connected to an electrode corresponding to hydrogel island 201b. As another example, the shield conductor 214 may have a contact location in the connector region to enable an electrical connection between the shield conductor 214 and an electrical connector. In operation, the shield conductor 214 may be driven to an instrument's ground, an instrument's reference voltage, or a right-leg drive output that measures and attempts to cancel common-mode signals on at least two electrodes. If a shield conductor 214 is connected to an electrode, the connection may be made with a via on electrode array 200 or through a connection made using an electrical connector and wiring external to electrode array 200.

Shield conductor 214 may be fabricated from metal or a semiconductor. The shield conductor 214 may be fabricated from at least one of gold, silver, platinum, palladium, rhodium, nickel, carbon, indium, tin, or copper. In another embodiment, the shield conductor 214 may be fabricated from at least one of gold, silver, or carbon. In a further embodiment, the shield conductor 214 may comprise silver/silver chloride. The shield conductor 214 may be deposited on a shield or on substrate 104 by any means know to the art, for example, by printing, silk screening, ink jet printing, sputtering, or printed circuit board fabrication methods. The shield conductor 214 may be silkscreened silver, silver/silver chloride, carbon black, or carbon nanotubes.

In some embodiments where a plurality of electrode arrays are used, the shield conductor 214 may be made of different colors of materials to visually differentiate the electrode arrays. For example, if a pair of electrode arrays was used, the first in the pair may have a carbon shield conductor and the second a silver or a silver/silver chloride shield conductor.

Figure 3:
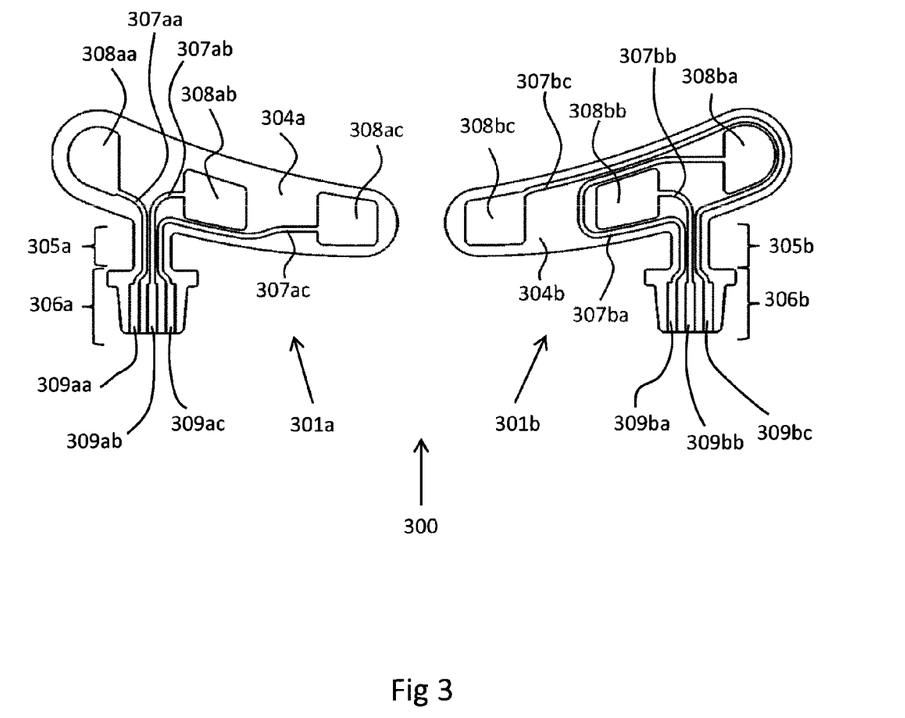
FIG. 3 is a view of one embodiment of a pair of electrode arrays, as seen from the patient side.
Figure 4A:
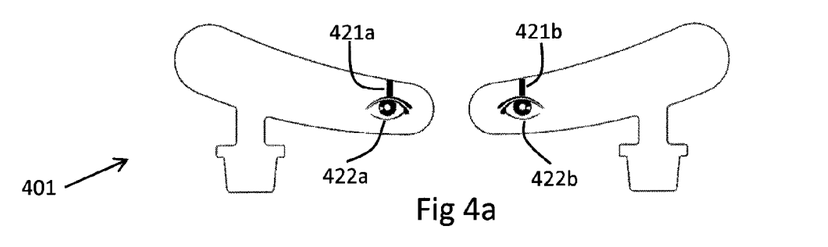
FIGS. 4a-4e are views of some embodiments showing sets of markings on pairs of electrode arrays, as seen from the operator side.
Figure 4B:
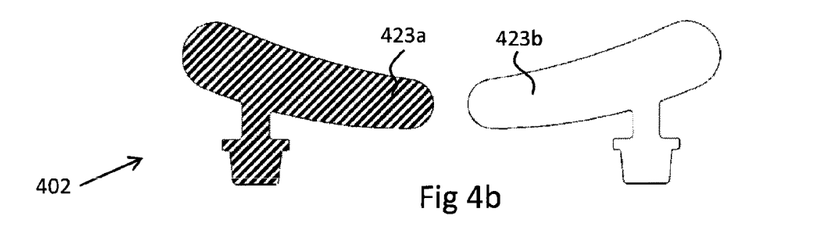
Figure 4C:
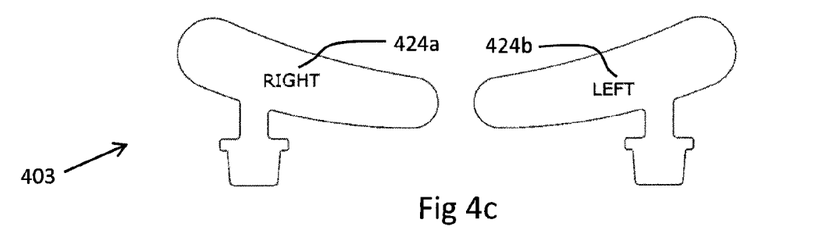
Figure 4D:
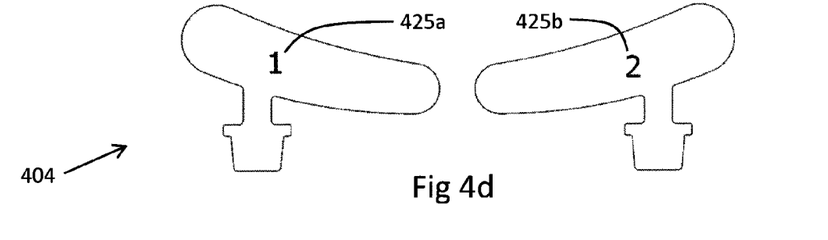
Figure 4E:
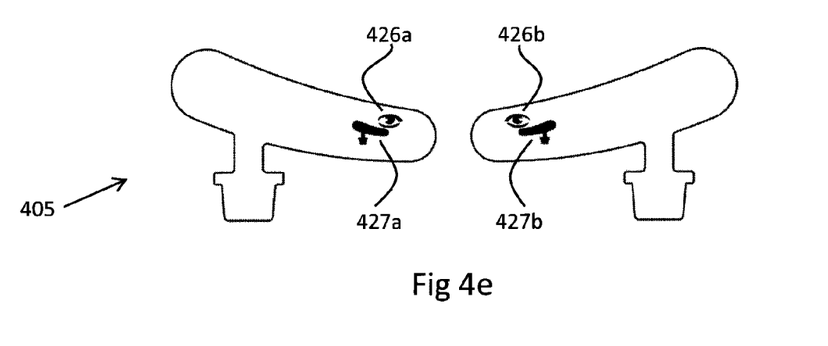

Turning now to FIG. 3, an exemplary embodiment of a pair of electrode arrays for monitoring physiological electric signals from the left and right sides of a human is shown. Pair 300 includes an electrode array 301a and an electrode array 301b. To better show the relation between elements, all features on electrode array 301a are designated with the letter "a" after the number, while all features on electrode array 301b are designated with the letter "b" after the number.

Both electrode arrays have a connector region (306a and 306b) as part of a flexible insulating substrate (304a and 304b). Electrodes 308aa, 308ab, 308ac are located on electrode array 301a, while electrodes 308ba, 308bb, and 308bc are located on electrode array 301b. Conductors 307aa, 307ab, 307ac provide an electrical connection between electrodes 308aa, 308ab, 308ac and contact locations 309aa, 309ab, and 309ac, respectively. Similarly, conductors 307ba, 307bb, 307bc provide an electrical connection between electrodes 308ba, 308bb, 308bc and contact locations 309ba, 309bb, and 309bc, respectively. Contact locations on electrode array 301a are found in connector region 306a while contact locations on electrode array 301b are found in connector region 306b. Both electrode arrays have optional torsion relief regions 305a and 305b, respectively and may optionally have other features described in electrode array 100 and/or electrode array 200.

The electrode arrays in pair 300 have their contact locations 309ba, 309bb, and 309bc in the same pattern so that one connector can alternatively make electrical connections to both electrode arrays. For example, the contact location 309aa may be located in the same position (left-most) as contact location 309ba. Further, it is possible to design a connector so that each connection that is made on electrode array 301a has an analogous connection in electrode array 301b. This property is ensured in the embodiment in FIG. 3 by making the connector region 306a the same shape as connector region 306b as well as having the same size and location of the contact regions on both electrode arrays. In alternative embodiments, the connector region shapes may differ between the electrode arrays as long as one connector can be used for both. Alternatively, the contact locations may differ in size or location between the electrode arrays as long as one connector can be used for both.

Pair 300 may be used, for example, to monitor physiological electric signals from the left and right sides of a patient. For example, electrode array 301a can be placed on the patient's left side and electrode 301b can be placed on the patient's right side. As a more specific example, electrode array 301a can be placed so that electrode 308ac is placed under the left eye and electrode 308aa is placed near the left temple. Similarly, electrode array 301b can be placed so that electrode 308bc is placed under the right eye and electrode 308ba is placed near the right temple. In these examples, the electrode placements map to the same contact location: for example, the electrode under the eye is electrically connected to the right-most contact region 309ac or 309bc for both electrode arrays.

Advantageously, instrumentation connected to either electrode array in pair 300 can interpret the electric signals in the same fashion. As a concrete example, suppose (1) electrode 308ac/308bc is placed on the skin under the left/right eye, respectively, and electrode 308aa/308ba is placed near the left/ right temple, respectively;
(2) a voltage difference is measured between contact location 309ac/309bc and contact location 309aa/309ba, respectively, and
(3) both eyes generate a positive electrical potential, then the voltage difference measured with electrode array 301a and electrode array 301b will both be positive, because of the mirror symmetry in pair 300.

Generally in pair 300, the relation between contact locations and electrode locations on the second electrode array is a mirror image to the relation between contact locations and electrode locations on the first electrode array. While not required, the substrate of the second electrode array may be a substantially mirror-image of the substrate of the first electrode array.

Analogous elements in pair 300 may be constructed in the same or a similar fashion to the corresponding elements found in electrode array 100 or electrode array 200, and may be fabricated from the same or similar materials. For example, electrodes in pair 300 can be constructed in the same manner as electrodes 108. Conductors in pair 300 can be constructed in the same manner as conductors 107.

The electrode arrays in pair 300 may optionally include hydrogels constructed in the same or similar fashion as those described in electrode array 100, and fabricated from the same or similar materials. The hydrogel islands of the second electrode array can be substantially mirror-images of the hydrogel islands of the first electrode array.

The electrode arrays in pair 300 may optionally include a shield constructed in the same or similar fashion as those described in electrode array 200, and fabricated from the same or similar materials.

The electrode arrays in pair 300 may be connected to each other or may not be connected to each other. Connecting has the potential advantage of having fewer ways in which an operator applying the electrodes to a patient can do so incorrectly, but has the potential disadvantage of being more restricted in accommodating differences in anatomy.

Turning now to FIG. 4, exemplary embodiments for marking a pair of electrode arrays are shown. In FIG. 4, pair 401, pair 402, pair 403, pair 404, and pair 405 are shown from the side opposite that of an electrode. Pairs 401, 402, 403, 404, and 405 have markings that differ on each electrode array in the respective pair. These marking can be used, for example, to indicate the desired placement orientation of the electrode arrays, the testing order of the electrode arrays, or other information. FIG. 4a shows markings that are representative of the anatomical part of the body that the electrode array should be placed near or on. For example, symbol 422a and symbol 422b show eyes that may indicate the portion of the electrode array that should be placed near the eye. Some embodiments may have additional symbols 421a and 421b to indicate more precisely the desired location of the electrode array. FIG. 4b shows markings where 423a has a distinctive pattern or coloring that differentiates it clearly from markings 423b. Color differences may result from shield conductors 214 of different materials; for example, marking 423a may comprise silver while marking 423b may comprise carbon. FIG. 4c shows markings where words are used to signify an electrode array 403 indented for the right side (424a) or for the left side (424b). FIG. 4d shows markings where numbers are used. Numbers may also indicate the test order: Number 425a may indicate the electrode array that should be tested first while number 425b may indicate the electrode array that should be tested second. FIG. 4e shows markings that are representative of the anatomical part of the body that the electrode array should be placed near or on. For example, symbol 426a and symbol 426b show eyes that may indicate the portion of the electrode array that should be placed near the eye. Some embodiments may have additional symbols 427a and 427b, which is the outline of the electrode array, to indicate more precisely the desired location of the electrode array relative to the anatomical part. Combinations of colors, words, symbols, and pictures are also contemplated.

These marked pairs of electrodes may have features of pair 300, or of electrode array 100, or of electrode array 200.

The size of the electrode arrays according to the embodiments described herein may be scaled to match the size of the intended patient. For example, an electrode array for a human infant may be smaller than an electrode array for a human adult.

While the figures in this disclosure have a similar shape to the electrode arrays depicted, other shapes are contemplated. For example, the pair of electrode arrays in FIG. 3 may be connected so as to reduce the likelihood of incorrect placement on a patient.

Methods of using the electrode arrays and pairs of electrode arrays of the invention are contemplated to measure electric signals from patients, for example, physiological electric signals. These signals may come from, for example, muscle, nerves, the heart, the brain, one or both ears, or one or both eyes. The methods can include obtaining electrodes arrays or pairs of electrode arrays, contacting the patient with the electrode arrays or pairs of electrode arrays, and measuring electric signals from at least one electrode. The reference potential for the voltage measurements can be another electrode or conductor that is capacitively coupled to the patient. The patient can be a human. Many devices are available that can be used to measure the electric signals, including for example generic data acquisition systems such as voltmeters and oscilloscopes, as well as data acquisition systems that have been designed for particular applications such as electroretinography (e.g., the LKC RETeval™ device or the LKC UTAS device, Gaithersburg, Md., USA).

The present invention is not to be limited in scope by the specific embodiments described herein. Indeed, various modification of the invention in addition to those described herein will become apparent to those skilled in the art from the foregoing description and accompanying figures. Such modifications are intended to fall within the scope of the claims.

What is claimed is:

1. An electrode array comprising:
   (a) at least two hydrogel islands, wherein at least two of the hydrogel islands have a corresponding electrode contacting said hydrogel island;
   (b) a flexible insulating substrate comprising an electrode region, a torsion relief region, and a connector region; and
   (c) conductors located on said substrate electrically connecting the electrodes to the connector region,
   wherein:
   all the electrodes are located in the electrode region;
   the connector region and the electrode region are connected together through the torsion relief region;
   the torsion relief region is narrower than the connector region and is connected to a long side of the electrode region, the long side of the electrode region being defined as the long side of the smallest rectangle that encloses all the electrodes; and
   the connector region comprises a tip region and a stop region, the tip region arranged at an edge of the electrode array and the stop region arranged adjacent to the tip region, the stop region being wider than the tip region.

2. The electrode array of claim 1, wherein the substrate further comprises edges in the connector region and some of the edges of the substrate in the connector region form guides that help in the positioning of a connector to make electrical contact with said conductors.

3. The electrode array of claim 2, wherein the electrode array is adapted for recording an electroretinogram.

4. The electrode array of claim 1, wherein a ratio of the largest distance between adjacent electrodes to the smallest distance between adjacent electrodes is less than 2.

5. The electrode array of claim 1, wherein the conductors and the electrodes are all located on one side of the substrate.

6. The electrode array of claim 1, wherein the hydrogel islands have a peel strength to stainless steel of no more than 1500 grams per inch and no less than 100 grams per inch.

7. The electrode array of claim 1, wherein the electrode array has exactly 3 electrodes.

8. The electrode array of claim 1, wherein the electrodes comprise at least one of gold, silver, or carbon.

9. The electrode array of claim 1, wherein the electrodes comprise silver/sliver chloride.

10. The electrode array of claim 1, wherein the electrode array is adapted for recording an electroretinogram.

11. A method of measuring an electric signal from a patient comprising:
    contacting the electrode array of claim 1 to the patient; and
    measuring the electric signal from at least one electrode.

12. The method of claim 11, wherein the electric signal is a potential difference between two electrodes in the electrode array.

13. The method of claim 12, wherein the electric signal is an electroretinogram.

* * * * *

UNITED STATES PATENT AND TRADEMARK OFFICE
CERTIFICATE OF CORRECTION

PATENT NO. : 9,510,762 B2
APPLICATION NO. : 14/426063
DATED : December 6, 2016
INVENTOR(S) : James J. Datovech et al.

It is certified that error appears in the above-identified patent and that said Letters Patent is hereby corrected as shown below:

In the Specification

Column 1, Lines 15-19:
"Inventions described herein were made with government support under grant 9R44EY021121 awarded by the National Institutes of Health, USA. Accordingly, per the terms and conditions of the grant, the U.S. government has certain license rights in the present application."

Should read:
--This invention was made with government support under grant number 9R44EY021121 awarded by the National Institutes of Health, USA. The government has certain rights in the invention.--

Signed and Sealed this
Sixteenth Day of December, 2025

John A. Squires
*Director of the United States Patent and Trademark Office*